(12) United States Patent
Vija

(10) Patent No.: US 10,772,582 B2
(45) Date of Patent: Sep. 15, 2020

(54) MULTI-MODAL EMISSION TOMOGRAPHY QUALITY BASED ON PATIENT AND APPLICATION

(71) Applicant: Siemens Medical Solutions USA, Inc., Malvern, PA (US)

(72) Inventor: Alexander Hans Vija, Evanston, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 233 days.

(21) Appl. No.: 15/925,902

(22) Filed: Mar. 20, 2018

(65) Prior Publication Data
US 2019/0290228 A1   Sep. 26, 2019

(51) Int. Cl.
*A61B 6/03* (2006.01)
*G01R 33/54* (2006.01)
*G01T 1/166* (2006.01)
*A61B 6/00* (2006.01)

(52) U.S. Cl.
CPC .............. *A61B 6/037* (2013.01); *G01R 33/54* (2013.01); *G01T 1/1663* (2013.01); *A61B 6/469* (2013.01); *A61B 6/481* (2013.01); *A61B 6/54* (2013.01)

(58) Field of Classification Search
CPC ........... A61B 6/037; A61B 6/54; A61B 6/469; A61B 6/481; A61B 6/032; A61B 6/5294; A61B 6/5205; A61B 6/465; G01R 33/54; G01R 33/48; G01T 1/1663
See application file for complete search history.

(56) References Cited

U.S. PATENT DOCUMENTS

| | | | |
|---|---|---|---|
| 6,573,718 B2 | 6/2003 | Rabe et al. | |
| 7,569,828 B2 | 8/2009 | Vija et al. | |
| 7,643,864 B2 | 1/2010 | Elgort et al. | |
| 8,629,404 B2 | 1/2014 | Vija | |
| 9,086,467 B2 | 7/2015 | Elgort et al. | |
| 2007/0118399 A1* | 5/2007 | Avinash | G06F 19/328 705/2 |
| 2013/0090946 A1* | 4/2013 | Foo | G06Q 50/22 705/3 |
| 2013/0267841 A1* | 10/2013 | Vija | A61B 5/0035 600/427 |
| 2017/0103512 A1 | 4/2017 | Mailhe et al. | |

(Continued)

*Primary Examiner* — Christine S. Kim

(57) ABSTRACT

For a multi-modal emission tomography system, an improved control system increases the likelihood of optimal image quality, satisfaction of physician goals, and/or avoids repetition in scanning and the corresponding increase in dose burden. The control system is divided into two or more arrangements. One arrangement receives goal information and outputs reconstruction settings and generic scan settings to satisfy the goal information. Another arrangement converts the generic scan settings to emission tomography system-specific scan settings, which are used to detect emissions. The separation of the arrangements allows independent operation so that different system-specific conversions may be used for different systems. Another possible arrangement performs a quality check on the detected emissions, allowing feedback for altering the system-specific scan settings to possibly avoid scan repetition and/or allowing feedforward for reconstruction to optimize the reconstruction settings based on the acquired data to be reconstructed.

19 Claims, 3 Drawing Sheets

(56) References Cited

U.S. PATENT DOCUMENTS

| | | | | |
|---|---|---|---|---|
| 2018/0061045 A1* | 3/2018 | Profio | ............... | G06T 11/008 |
| 2018/0144214 A1* | 5/2018 | Hsieh | ............... | G06K 9/6265 |
| 2018/0253531 A1* | 9/2018 | Sharma | ............... | G16H 30/20 |
| 2018/0315223 A1* | 11/2018 | Vija | ............... | G06T 11/005 |
| 2018/0330233 A1* | 11/2018 | Rui | ............... | G06F 17/5009 |
| 2019/0046813 A1* | 2/2019 | Zhou | ............... | G16H 40/63 |
| 2019/0142338 A1* | 5/2019 | Fang | ............... | G06N 3/0454 |
| | | | | 600/408 |
| 2019/0231224 A1* | 8/2019 | Rupcich | ............... | G06T 7/97 |
| 2019/0231288 A1* | 8/2019 | Profio | ............... | A61B 6/42 |
| 2019/0354882 A1* | 11/2019 | Sharma | ............... | G06N 5/04 |
| 2020/0005088 A1* | 1/2020 | Joy | ............... | G06N 3/04 |

* cited by examiner

MULTI-MODAL EMISSION TOMOGRAPHY QUALITY BASED ON PATIENT AND APPLICATION

BACKGROUND

The present embodiments relate to emission tomography or other nuclear medical imaging. Example tomography imaging modalities include single photon emission computed tomography (SPECT) and positron emission tomography (PET). A radioactive substance is administered to a patient. An imaging scanner detects the γ-radiation emitted from the patient. The detected emissions are tomographically reconstructed to generate an image object of locations of the emissions in a patient.

Different scans and reconstructions are available, depending on various factors related to the goals of the physician, capabilities of the scanner, and characteristics of the patient. With the advancements in acquisition and reconstruction technology in multi-modal emission tomography, the number of parameters to be adjusted has grown. While multi-modal emission tomography may result in better or more useful information, the added modality scan results in even more settings to be controlled. Manual setup, expert setup, or standardized setup of reconstruction and scanning are typically used, but may not be optimum for the goals, capabilities, and characteristics. It is time consuming and difficult to optimize for each examination. In clinical set up, one tries to set up standardized scan and reconstruction protocols and significant adaptations are discouraged. If adaptation is required, an expert user may be consulted, yet even that user may not have all the information and know-how to optimally set up the examination (e.g., protocols). This circumstance exists for each application and patient. The result is sub-optimal image quality, repeated scans, and/or higher dose burden to the patient just to sub-optimally satisfy the goals.

SUMMARY

By way of introduction, the preferred embodiments described below include methods, systems, and non-transitory computer readable media for controlling operation of a multi-modal emission tomography system. To increase the likelihood of optimal image quality, satisfy physician goals, and/or avoid repetition in scanning and the corresponding increase in dose burden, an improved control system is provided for emission tomography. The control system is divided into two or more arrangements. One arrangement receives goal information and outputs reconstruction settings and generic scan settings to satisfy the goal information. Another arrangement converts the generic scan settings to emission tomography system-specific scan settings, which are used to detect emissions. The separation of the arrangements allows independent operation so that different system-specific conversions may be used for different systems. Another possible arrangement performs a quality check on the detected emissions, allowing feedback for altering the system-specific scan settings to possibly avoid scan repetition and/or allowing feedforward for reconstruction to optimize the reconstruction settings based on the acquired data to be reconstructed.

In a first aspect, a method is provided for controlling operation of a multi-modal emission tomography system. An input of a type of emission tomography scan and a goal for the emission tomography scan is received. A first machine-learnt network generates first settings for reconstruction parameters and second settings for the emission tomography scan. The generation is based on the type, the goal, and patient information, and the second settings are generic to the multi-modal emission tomography system. A second machine-learnt network determines third settings for the emission tomography scan from the second settings. The third settings are specific to the multi-modal emission tomography system. The multi-modal emission tomography system detects emissions from a patient using the third settings. An emission tomography image of the patient is created from the detected emissions. The creation is a function of the first settings.

In a second aspect, a nuclear imaging system includes a first processor configured to determine a reconstruction and a scan based on a patient characteristic and an application provided by a physician. The first processor or a second processor is configured to determine settings for scan parameters from the scan. A detector for detecting signals from a patient using the settings, where the settings are specific to the detector. A reconstruction processor is configured to reconstruct an image of the detected signals from the patient with the reconstruction, and a display is configured to display the image.

In a third aspect, a method is provided for controlling operation of a multi-modal emission tomography system. The multi-modal emission tomography system is controlled with: an application analysis module configured to recommend scan information based on a patient state and medical information from a physician, an acquisition set-up module configured to recommend settings for acquisition specific to the multi-modal emission tomography system based on the scan information, and a data quality assessment module configured to feedback to the acquisition set-up module for a change in the settings for the acquisition. Emissions from the patient are detected using the settings. An emission tomography image is generated from the detected emissions.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

To ensure multi-modal data quality based on application and patient, a control arrangement is provided for multi modal emission tomography. Patient specific setup enables a precise medicine framework that systematically defines and controls a clinical workflow to deliver images that are optimal for the clinical task. The control arrangement includes two or more (e.g., three) modules. An Application Analysis Assistant (AAA) defines the workflow and quality requirements. An Acquisition Setup Assistant (ASA) defines scan requirements specific to the emission tomography system. A Multi-modal Data Quality Assistant (MMDQA) checks data from the scanner and suggests action.

This control framework in multi modal imaging is comprehensive and driven by clinical task. The clinical task is linked to the technology layer, so the linking (e.g., ASA) may deal with the often-changing capabilities of the emission tomography system without requiring change in other parts of the control arrangement. The control framework is data driven and may optionally use artificial intelligence and/or data analytics.

Figure 1:
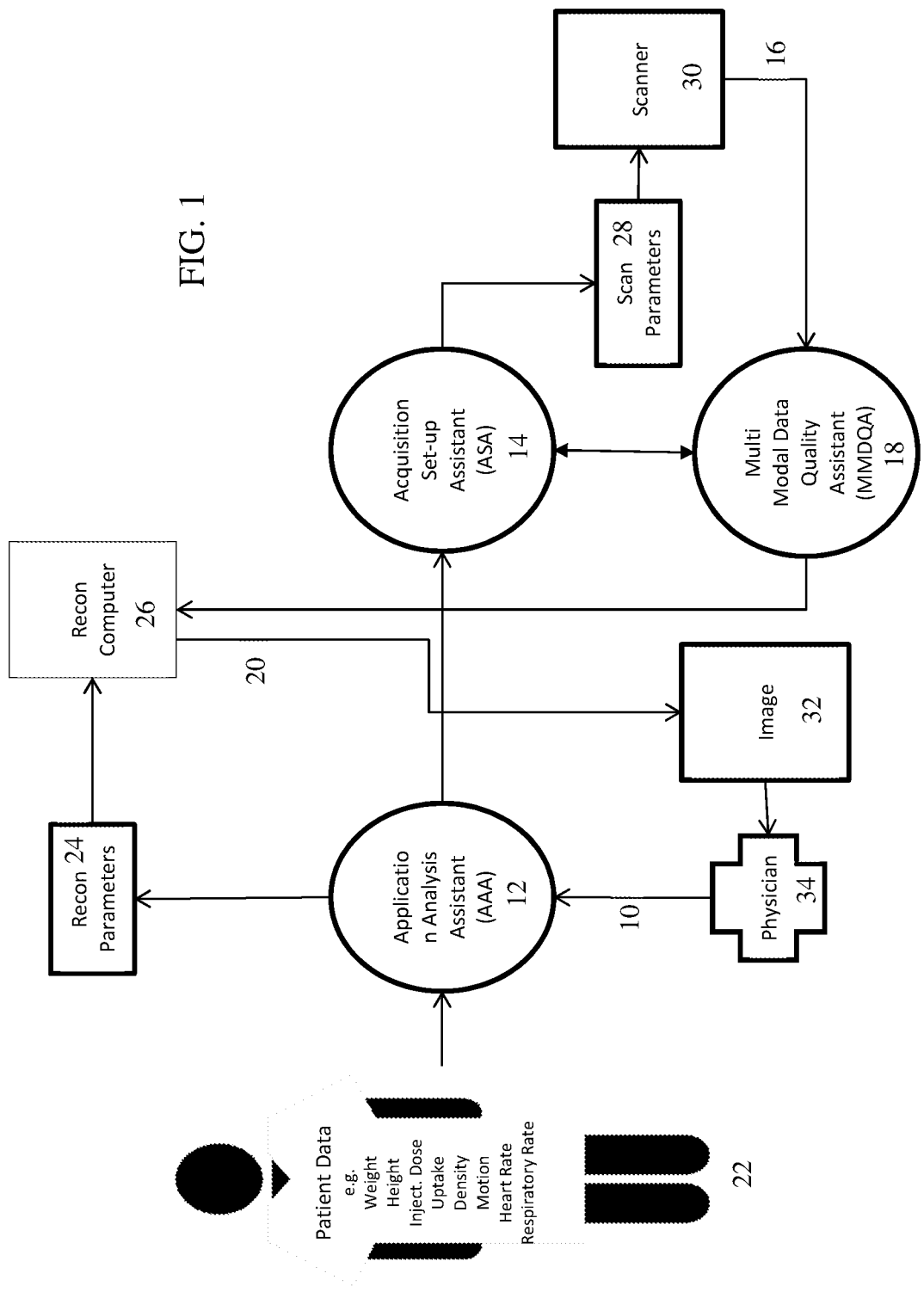
FIG. 1 illustrates one embodiment of a control arrangement for controlling operation of a multi-modal emission tomography system.
Figure 2:
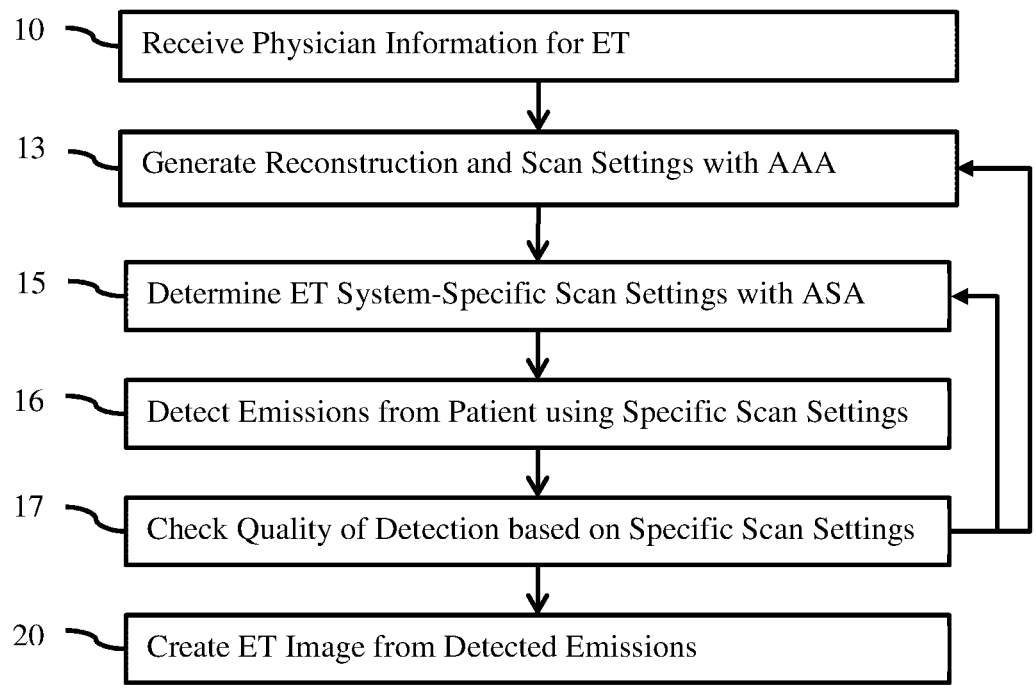
FIG. 2 is a flow chart diagram of one embodiment of a method for controlling operation of a multi-modal emission tomography system.

FIG. 1 shows one embodiment of the control framework. The control framework is for controlling operation of a multi-modal emission tomography system. FIG. 2 shows one embodiment of a method for controlling operation of the system using the control framework of FIG. 1. Separate control arrangements (e.g., AAA, ASA, and/or MMDQA) are used to control the system, handling different aspects relating the physician goals, patient characteristics, and controlled system to generation of a desired image while avoiding or limiting rescanning, satisfying the goals, and/or providing an image optimizing the system capabilities to goals.

Additional, different, or fewer acts may be provided. For example, the check for quality (e.g., MMDQA) is not performed. As another example, acts for inputting, verifying, patient positioning, and/or activating the scan are provided. The feedback from act 17 to act 15 and/or 13 may not be provided. The acts are performed in the order shown (top to bottom or numerical in FIG. 2), but other orders may be used.

Figure 3:
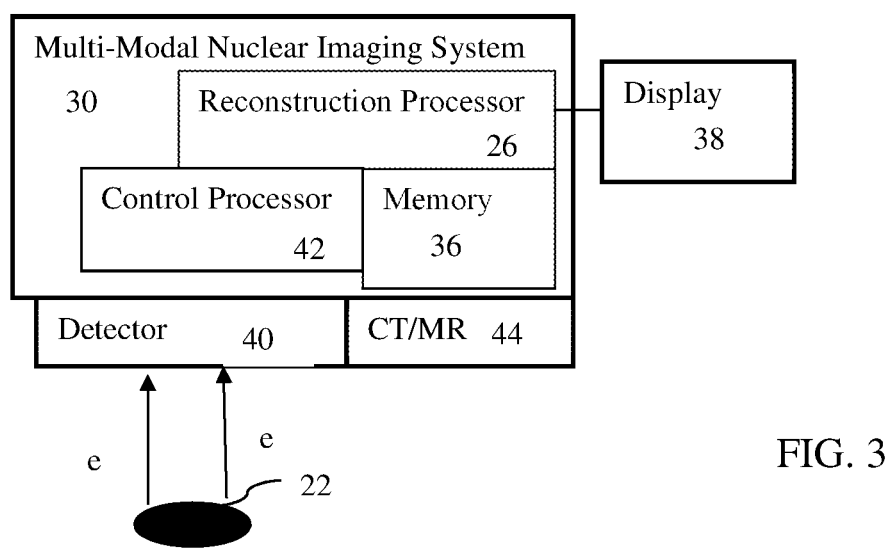
FIG. 3 is a block diagram of a nuclear imaging or emission tomography system, according to one embodiment.

The control framework and method are implemented by the system of FIG. 3 or another system. A multi-modal emission tomography system (e.g., computed tomography with PET or SPECT) performs the acts of the method, implementing the control arrangements. Alternatively or additionally, a remote server or workstation handles some or all the control framework (e.g., AAA, ASA, and/or MMDQA) and the tomography system is controlled by outputs from the remote server or workstation. Other distributions of control amongst a computer network may be used.

The control framework is formed by the multiple arrangements. Each arrangement operates independently of the others. One arrangement may output to another and/or receive output from another arrangement but processes the input to derive the output without other control or reliance on the other arrangements than an input.

The arrangements are modules, such as hand coded instructions. In one embodiment, each of the arrangements are machine-learnt networks. Using many samples (e.g., tens, hundreds, or thousands) of inputs and corresponding desired or ground truth outputs, the network is trained to relate any input combination to a desired output. Any architecture and corresponding type of machine learning may be used. For example, a neural network architecture is used for deep learning. In one embodiment, a deep convolutional network, such as four layers of convolution and max pooling (e.g., in an every other layer arrangement), is used. Other architectures with different numbers of layers, different types of layers, and/or different orders of layers may be used. The deep learning learns convolution filter kernels and/or other parameters of the neural network (e.g., node connections and weights) relating the input to the output using the samples. Any optimization function for training may be used, such as a loss function. A machine, such as a computer, learns the relationship of the input to the output based on the assigned architecture. The training results in a machine-learnt network that outputs based on inputs. The arrangement is configured by the learnt network and/or hand coding.

Separate machine-learnt networks are provided for each of the arrangements, such as the AAA 12, ASA 14, and MMDQA 18. In alternative embodiments, one network is trained to implement two or more of the arrangements.

The AAA 12 is an application analysis module configured to recommend scan information based on a patient state and medical information from a physician 34. The scan information is generalized or not specific to any particular emission tomography (ET) scanner. The AAA 12 is also configured to recommend reconstruction settings 24 based on the patient state and the medical information. The AAA 12 helps to set up application and patient specific acquisition and reconstruction parameters 24. Based on a clinical question, physician goal, and/or patient information, the AAA 12 recommends acquisition and reconstruction workflow and parameters 24. For example, the physician inputs a clinical question as a type of imaging (e.g., level of myocardial perfusion) and a goal of four minutes of scan time. The patient weight and/or height are provided. The AAA 12 recommends a dose, collimator arrangement, scan time, and size of scan region for the scan settings and motion correction with a type of reconstruction less susceptible to motion as the reconstruction parameters based on the inputs.

The ASA 14 is an acquisition set-up module configured to recommend settings 28 for acquisition specific to the multi-modal emission tomography system 30 based on the scan information output by the AAA 12. Based on application assistant processing with or without patient data, optimal parameters 28 for scanning with the specific system 30 are output. The patient data may include height, heart rate and/or respiratory rate. The settings 28 to configure the emission tomography system 30 to scan 16 the patient 22 are determined. For example, the dose, collimator arrangement, scan time, and size of the scan region with the heart rate of the patient are input. The ASA 14 outputs specific settings 28 for scanning the patient 22, such as a step size, spread of camera motion, bed position, and collimator settings for scanning the patient.

The ASA 14 may be adaptive. Feedback from the MMDQA 18 or other source may be used to alter one or more of the settings 28 during an ongoing scan. The settings 28 are output before and/or during the scan.

The MMDQA 18 is a data quality assessment module configured to feedback to the acquisition set-up module for a change in the settings 28 for the acquisition. The feedback is based on the detected emissions (e.g., projection, tomo, gated-tomo, or dynamic-tomo data, such as sinograms) and/or any data from the other modality (e.g., reconstructed volume from a CT or MR scanner). Other possible inputs include list mode (LM) data, the scan information from the AAA 12, the scan settings 28 from the ASA 12, application information (e.g., inputs 10 from the physician), patient information, and/or the reconstruction settings 24.

The MMDQA 18 may be configured to output a mitigation, such as indicating a score or other information used by the ASA to change the scan parameters 28. The scan parameters 28 are changed to provide the desired characteristics of the detected emissions for optimized reconstruction. Other mitigations may be a change to or establishment of reconstruction settings 24, repeating a scan of the patient 22, and/or other alteration.

The MMDQA 18 ensures that the acquired multi modal data is acceptable for reconstruction during and/or after acquisition. In one embodiment, one or more quality scores are used. If data becomes corrupted, then the score reflects the corruption, and the mitigation is performed. For example, the MMDQA 18 evaluates the image quality of SPECT/CT acquisition data and automatically generates quality scores to help a technologist decide whether to accept the acquisition or to perform a rescan.

Various checks and/or scores may be provided. For example, a CT data truncation check and/or a SPECT data truncation check are performed. The total counts distribution as a function of angles and/or regional count densities may be checked. The number of views and/or angular sampling may be checked. The sinograms may be analyzed, such as a statistical analysis, and/or the view consistency may be checked. The system quality control status, detector abnormality, or other operational outputs of the system 30 may be checked. The MMDQA 18 outputs, for each check, a score, feedback, information used to mitigate, and/or a mitigation based on the inputs.

In one embodiment, the MMDQA 18 treats the data quality assessment task as a classification problem of three classes—good, acceptable, and poor. Any ranges may be provided, such as ten classes. A threshold is applied to determine whether a given mitigation is warranted, such as no rescan required where a given score or combination of scores is below or above the threshold. The threshold or set of thresholds may be application and/or mitigation dependent.

Referring to FIG. 2, the control arrangement of FIG. 1 is used for scanning a patient to optimize the resulting image. A method for controlling operation of the multi-modal emission tomography system 30 is provided. A procedure uses the three control arrangements (AAA 12, ASA 14, and MMDQA 18) to optimize more reliably than a radiologist.

In act 10, a control or image processor receives input. The input is received from a user input device, memory, and/or communications network interface.

The input is information from a treating or ordering physician or a radiologist. The input is a type of emission tomography scan and/or other goal for the emission tomography scan. The type of emission tomography scan is an application, such as anatomy or disease-based application. For example, cardiology, neurology, oncology, or general types are possible. More specific types may be input, such as a myocardial perfusion type of the cardiology type of emission tomography scan. Other identifications of the application may be used, such as identifying the anatomy of interest.

Other goals or information may be input. For example, patient information is received. The age, weight, height, sex, and/or other characteristic of the patient is received. As another example, a dose, type of isotope available, or other physician-related input may be provided. A goal, such as the total amount of time to scan (e.g., 5 minutes for a claustrophobic patient) may be used. Another goal may be the desired resolution, contrast, or resolution and contrast tradeoff.

Any information used to determine reconstruction settings or generic scan settings is input. The AAA 12 is a physician tool. General goals, application, and/or patient information is input to provide recommended reconstruction and scanning to achieve the goals.

In act 13, the control or image processor implements or operates the AAA 12. For example, a machine-learnt network generates settings for reconstruction parameters and settings for the emission tomography scan based on the input information. The control or image processor inputs the received inputs or information derived from the received inputs into the machine-learnt network, which generates the outputs in response. For example, the type of emission tomography scan (e.g., application), the goal (e.g., time limit) and/or patient information (e.g., weight, height, and/or sex) are input, and the machine-learnt network generates the output reconstruction settings 24 and scan settings. The AAA 12 analyzes the physician's medical information need for the image and relevant patient state and recommends an optimal set of parameters to the ASA 14 and the reconstruction computer 26.

The reconstruction parameters or settings 28 define or configure the reconstruction from the detected emissions into object or image space. The reconstruction is defined by the type of reconstruction, a relative contrast-to-resolution, and a stop criterion. Different types of reconstruction include filtered back-projection, iterative reconstruction, multimodal reconstruction, Maximum Likelihood Expectation Maximization (ML-EM), Ordered Subset Expectation Maximization (OSEM), penalized weighted least squares (PWLS), Maximum A Posteriori (MAP), and/or non-negative least squares (NNLS). The relative resolution and contrast may be based on separate parameters or a parameter balancing the tradeoff. The stop criterion may be a number of iterations, a sufficiency of a statistical measure (e.g., chi-squared criterion), or other thresholds, measurements, or limitations to end reconstruction.

Other parameterizations of reconstruction may be used, such as image width, reconstruction strategy, use of A-priori information (e.g., CT or MR information), accuracy vs. speed parameter, smoothing parameters, motion correction parameters, iteration number, and/or sub-set processing.

The scan settings are generic to the specific multi-modal emission tomography system 30. For example, the AAA 12 outputs the dose, collimator configuration, time to scan, region to scan, isotope being used, and/or other information generally guiding the scan to provide the optimum information given the goals. The scan settings output by the AAA 12 are generic to the different types or capabilities of emission tomography systems. Rather than being specific values for parameters used during an actual scan, the general scan settings provide goals for the scanning. The generic scan settings are not values of variables used to actually control the multi-modal emission tomography system during scanning (e.g., not a gamma camera step size or dwell time). One or more of the scan settings output by the AAA 12 may be specific, such as the isotope to be used, to the scan for the patient. By being generic to the specific scanner 30, different scanners 30 may receive the scan settings and then implement the scanning based on the generic scan settings.

In act 15, the control or image processor implements or operates the ASA 14. For example, a machine-learnt network determines settings 28 for the emission tomography scan from the scan settings output by the AAA 12. The scan settings 28 output by the ASA 14 are specific to the multi-modal emission tomography system 30. The system-specific scan settings 28 are values of variables used to control the actual scan. The generic scan settings are translated to scan settings 28 for configuring and operating the specific scanner 30. Patient information, physician input information, feedback from the MMDQA 18, and/or other information may or may not be used to translate. The settings to operate both modalities (e.g., SPECT and CT) are determined.

In one embodiment, the gantry speed, x-ray source voltage, range of motion, x-ray filter, x-ray focus, number of projections, CT reconstruction, or other CT scan settings for the specific CT system are determined. The step size, spread (e.g., range of motion of the gamma camera), and/or a collimator position for the specific SPECT system are determined. Thresholds, filtering, or other processing of detected data may be established as settings for scanning. The ASA 14 recommends settings for all relevant acquisition parameters for the specific hardware and software present for scanning the patient 22. In one embodiment, a SPECT system 30 includes scan parameters 28 for a start time, duration, matrix size, pixel size (zoom), rotation direction, angular sampling, temporal sampling, orbit (e.g., non-circular orbit close to the patient or circular orbit at a radial distance from the patient), and/or acquisition method (e.g., continuous vs. step-and-shoot). Different systems may have different parameterizations (e.g., settable parameters to control the scan), so the ASA 14 is specific to the system.

In act 16, the emission tomography system 30 detects emissions from the patient using the settings. The multi-modal emission tomography system is configured by the system-specific settings output by the ASA 14. Once the scan parameters 28 are accepted by the user and the patient 22 has been prepared and readied, the scan commences, and thus data is acquired. Rather than having user verification, the scan may be started automatically based on the scan parameters 28 and confirmation of proper patient positioning.

The emission tomography system 30 scans the patient based on the settings 28. For example, the start position, dwell time, step size, collimator position, and/or other aspects of a SPECT scan control the operation of the system 30. After ingesting or injecting a radiotracer into the patient 22, the patient 22 is positioned relative to a detector, and/or the detector is positioned relative to the patient 22. Emissions from the radiotracer within the patient 22 are detected over time. A collimator in front of the detector limits the direction of photons detected by the detector, so each detected emission is associated with an energy and line of response (e.g., a cone of possible locations from which the emission occurred). For SPECT, the detector may be rotated or moved relative to the patient, allowing detection of emissions from different angles and/or locations in the patient, or any other way of creating a tomographically suited dataset from single photon emissions. In PET embodiments, the detector is formed in a ring so that coincidence is used to detect the same emission from different directions along the lines of response. Similarly, the other modality (e.g., CT) is controlled by settings to scan.

The emission detector includes direct detection with CZT or indirect conversion (e.g., NaL, LSO layered scintillation crystal) using photomultiplier tubes, SiPM, or other photon detectors. For SPECT, the photon detectors are arranged along a rectangular or other grid to provide a two-dimensional planar array for detecting gamma radiation. For PET, the detectors are arranged in a ring around a patient. Other types of detectors may be used, such as any gamma detector.

In act 17, the control or image processor implements or operates the MMDQA 18. For example, a machine-learnt network checks a quality of the detected emissions and/or anatomy data. Other inputs to the MMDQA 18 may be the generic scan settings from the AAA 12, reconstruction settings 24 from the AAA 12, patient information, data from the other modality (e.g., CT data), and/or the system-specific scan settings 28 from the ASA 14. The MMDQA 18 receives the inputs or the inputs are applied to the MMDQA 18.

The MMDQA 18 checks for data quality and/or proper operation of the scanner 30. For example, a number of counts per view and/or a circular orbit of the multi-modal emission tomography system is checked. Other checks may be performed, such as statistical analysis of the detected emissions. In other embodiments, the MMDQA 18 receives and checks a reconstruction from the reconstruction computer 26, such as checking the data of an initial reconstruction performed before completion of the scanning. In yet other embodiments, the MMDQA 18 receives an image rendered from a reconstruction and checks the image.

In response to the input information, the MMDQA 18 generates one or more outputs, such as scores, feedback, and/or mitigations. The score may be used as feedback, to determine the feedback to use, and/or to determine a mitigation. In a feedback from act 17 to act 15, the MMDQA 18 indicates the insufficiency with a score, provides feedback to the ASA 14 (e.g., in the form of a score or a request to position the camera at the location with insufficient count), and/or provides a mitigation in the form of a time, detector position, and/or other information. The ASA 14 responds to the score, feedback, or mitigation by altering the scan settings 28. For example, a further scan with the detector at a previously used position is added. As another example, the dwell time at one or more detector positions may be increased or decreased. The step size, range of detector positions, and/or total scan time may be changed in response to output from the MMDQA 18. As data is acquired, the data is analyzed with the MMDQA 18, which could send back to the ASA 14 feedback to adjust the scan to adapt to changing situations. The ASA 14 adapts the scan, and the scanner adapts its operation. Further emissions are detected in act 16 using the altered scan settings 28.

In the feedback from act 17 to act 13, the MMDQA 18 indicates any poor quality. The AAA 12 may respond with different or altered reconstruction settings 24. Acts 15-16 may not be repeated. Alternatively, the AAA 12 changes one or more generic scan settings, so acts 15-16 are repeated with changes due to the alteration of the generic scan settings.

In alternative or additional embodiments, the quality check of act 17 is performed once the scan is complete. Once the scan is completed, the MMDQA 18 analyses the multi-modal data needed for reconstruction for feasibility to achieve the goal set by AAA 12. Based on the check, the patient is released from the bed and/or a mitigation is suggested. For example, feedback is provided to the ASA 14 for a portion or all of the scan to be repeated with the same or different scan settings 28. The patient 22 remains on the scan bed, avoiding additional dose added due to scanning again in a different appointment. Based on the AAA 12, ASA 14 and/or MMDQA 18, once the patient is released, the user can have high confidence that the reconstruction engine will deliver adequate images for a specific task.

In act 20, the reconstruction processor 26 generates an emission tomography image 32 from the detected emissions. For multi-modal reconstruction, the image is generated from the detected emissions and the anatomy data from the other modality (e.g., CT or MR).

The reconstruction uses the reconstruction settings 24. The type of reconstruction, the values of variables used in reconstruction, stop criterion, motion correction settings, and/or other information used to control reconstruction are defined by the reconstruction settings 24. The object space representation of emissions from the patient 22 is reconstructed from the detected emissions using the reconstruction settings 24 from the AAA 12 and/or MMDQA 18.

The reconstruction processor 26 may adapt to the detected emissions and/or anatomy data (e.g., CT or MR data). For example, an output score or feedback of the MMDQA 18 indicates a data characteristic. The reconstruction settings 24 are adjusted to account for the characteristic. Alternatively, a setting is established based on the characteristic and without a value from the AAA 12. One or more reconstruction settings 24 may be established based on the scan data from either or both modalities. In other embodiments, the feedback from the MMDQA 18 is to the AAA 12. The reconstruction engine is in communication with AAA 12, so receives the altered reconstruction settings 24 from the AAA 12.

Computed tomography implements reconstruction to determine a spatial distribution of emissions from the detected lines of response. The projection data represents the detected emissions. The quantity or amount of uptake for each location (e.g., voxel) may be estimated as part of the reconstruction. The nuclear imaging system may estimate the activity concentration of an injected radiopharmaceutical or tracer for the different locations.

Any now known or later developed reconstruction methods may be used, such as based on Maximum Likelihood Expectation Maximization (ML-EM), Ordered Subset Expectation Maximization (OSEM), penalized weighted least squares (PWLS), Maximum A Posteriori (MAP), multi-modal reconstruction, non-negative least squares (NNLS), or another approach. Different types of reconstruction have different strengths and weaknesses. Different processes for dealing with motion or other sources of distortion may be used for a same method, resulting in yet other types of reconstruction. Some types of reconstruction may take longer or have lesser resolution, such as results from dealing with motion.

The reconstruction is iterative. The image reconstruction processor 26 uses a system matrix or projection operators to describe the properties of the nuclear imaging system and uses an iteratively improved data model to calculate the image object based on the data set of detected emissions. Anatomical segmentation may be used in the reconstruction to improve assignment of locations of emission based on anatomy. The iterative reconstruction forward projects a current estimate of the object or image (e.g., object or image space) to projection or data space using a system matrix or forward projector operators representing the detection. Since the detected emissions are in a projection space (e.g., generally known location in two-dimensions but not three), the forward projection of the current volume is compared to the detected or measured emissions. This comparison is tested for accuracy with a merit function (e.g., NNLS, or Mighell's modified chi square). If sufficiently accurate and/or having no further increase in accuracy, the iteration ceases, and the current image object is output as the reconstructed image object. If the merit function indicates insufficient or improving accuracy, a difference or residual between the forward projection and the detected emissions is backward projected. This backward projection provides a gradient or change for the image object. The direction and step size are determined for the change and is applied to update the image object. The process is then repeated for another iteration of the reconstruction. Once complete, an image object, which may be an N-dimensional image object (typically N=3 in medical imaging applications), results.

To display an emission tomography image on a display screen, the reconstructed object is rendered to the display. Where the object is reconstructed as three-dimensional, then three-dimensional rendering is used to collapse the object to a two-dimensional image. Surface, volume, path tracing, ray casting, alpha blending, maximum intensity projection, or other volume rendering may be used.

The generated image is mapped to display values, such as RGB color values. The mapped values are buffered and used to display the emission tomography image on the screen of the display. The image may include anatomical information, such as overlaying the emission tomography image on a CT or MR image. Alternatively, the emission tomography image is displayed without the CT or MR image.

Due to the use of the control arrangement, the scan and reconstruction more likely optimizes the image to satisfy the goal or goals of the physician. The resolution or contrast tradeoff, field of view, number of counts used, time to scan, and/or image quality are more likely what the treating physician desires and/or are more likely to be appropriate for the application and patient than using standardized or application default scanning. The image quality to perform a detection task for higher than background or colder than background lesions and/or the quantitative accuracy and precision of a volume of interest are optimized given the tracer, patient habitus, application and clinicians criteria to reject the null hypothesis. Rather than relying on a user who may or may not provide the optimized image for a given scan, the control arrangement allows entry of the application, patient information, and/or goal or goals and provides the optimized image, maximizing the image content relative to the goal, application, and/or patient given any constraints. This approach allows updates or different capabilities to be provided without the user having to know of, remember to use, and/or know how to use all the various capabilities. Due to the separation of the AAA 12 from the ASA 14, the emission tomography system 30 may change or be altered without having to re-create the entire control arrangement. Instead, the ASA 14 is relearnt.

FIG. 3 shows one embodiment of a nuclear imaging system 30. The system 30 is a PET, SPECT, or other multi-modal emission tomography imaging system for detecting emissions due to radioactive decay in a patient assisted by anatomical information from another modality. The nuclear imaging system 30 may provide qualitative or quantitative imaging.

The system 30 implements the method of FIG. 2, the control arrangement of FIG. 1, or other method. The treating physician enters an application, goal, or other indication of the diagnostic, prognostic, or therapeutic reasons for performing emission tomography for the patient. Patient information is entered. Reconstruction and generic scan settings are determined based on the physician request and patient information. The generic scan settings are translated into system-specific scan settings. The detected emissions and other scan output may be checked for quality. As a result, an image optimized to the patient, the system 30, and the physician reasons for imaging is generated without requiring the operator to use a less optimized standard or default settings.

The multi-modal nuclear imaging system 30 includes a control processor 42, a reconstruction processor 26, a memory 36, a display 38, a detector 40, and a CT/MR system 44. The control processor 42, reconstruction processor 26, memory 36, and/or display 38 are part of the imaging system 30 with the detector 40, part of the emission tomography part of the system 30, part of the CT/MR part of the system 30, or are separate (e.g., a computer or workstation). Additional, different, or fewer components may be provided. For example, the system 30 is a computer without detector 40 and/or separate from the CT/MR system 44. As another example, user input, patient bed, x-ray scanner, or other nuclear imaging-related devices are provided. Other parts of the system 30 may include power supplies, communications systems, and user interface systems.

The CT/MR system 44 is an anatomical imaging modality. The CT/MR system is one of CT or MR but may be another anatomical medical imaging modality (e.g., ultrasound). Anatomical information is acquired by scanning with x-rays or magnetic resonance. The anatomical information may be used for emission tomography, such as using segmentation of anatomy or tissue type for reconstruction of emissions with a greater spatial resolution.

The control processor 42 a general processor, digital signal processor, graphics processing unit, application specific integrated circuit, field programmable gate array, digital circuit, analog circuit, combinations thereof, or other now known or later developed device for controlling the operation of the system 30. In one embodiment, a single hardware processor as the control processor 42 implements the various control arrangements (e.g., AAA, ASA, MMDQA). In other embodiments, different parts of the control are hosted by or implemented by different processors, such as a server or workstation. The control processor 42 is a distributed network of interconnected processors. The control processor 42 is configured by software, firmware, and/or hardware to perform specific acts.

The control processor 42 is configured to determine a reconstruction and a scan based on a patient characteristic and an application provided by a physician. The AAA is implemented. The reconstruction is a type of reconstruction and/or other reconstruction settings. The scan is a type of scan and/or other generic scan settings.

In one embodiment, the control processor 42 receives input of physician goals, other application information, and/or patient information. The input information is applied to a machine-learnt network. In response to input to the network, the network outputs the scan and reconstruction.

The control processor 42 is configured to determine settings for scan parameters from the scan. The ASA is implemented. The scan from the control processor 42 is translated into detector-specific scan settings. Emission tomography system-specific scan settings are determined. CT/MR-specific scan settings are also determined.

In one embodiment, the control processor 42 receives the scan information from the AAA and/or patient information. This input information is applied to a machine-learnt network. In response to the input to the network, the network outputs system-specific scan settings.

The system-specific scan settings are used to scan the patient. The detector 40 is a gamma camera connected with a gantry. The gamma camera is a planar photon detector. Any now known or later developed gamma camera may be used. The gantry rotates the gamma camera about the patient. Alternatively, the detector 40 is a ring of crystals or scintillators with photomultiplier tubes or other optical detectors. Other structures of detectors may be used. Other components may be provided, such as a collimator. The detector 40 and other parts of the emission tomography system are configured to perform the scan of the patient 22 by the settings or values of the scan parameters.

The nuclear imaging system 30, using the detector 40, detects emissions from the patient 22 for measuring uptake or physiological function. During scanning of a patient 22, the detector 40 detects emission events, e. The emissions occur from any location in a finite source (i.e., the patient 22). The radiotracer in the patient 22 migrates to, connects with, or otherwise concentrates at specific types of tissue or locations associated with specific biochemical reactions. Thus, a greater number of emissions occur from locations of that type of tissue or reaction. The emission events are detected at different positions or angles relative to the patient, forming lines of response for the events. With a ring of detectors of PET, the emissions are detected along the lines of response without movement of the detector 40. The patient bed may move to define a field of view relative to the patient.

The control processor 42 is configured to check the detected signals. The MMDQA is implemented. Data quality from the data of the detector 40 and/or the CT/MR system 44 is checked. Operation of the detector 40 or other parts of the emission tomography system may be checked.

In one embodiment, the control processor 42 receives the detected emissions, anatomy data (CT or MR data), detector 40 operation measurements, scan settings, and/or patient information. This input in provided to a machine-learnt network. In response, the network outputs scores, feedback, and/or mitigation. For example, feedback is provided to ASA to re-determine the settings based on the check.

The reconstruction processor 26 is a general processor, digital signal processor, graphics processing unit, application specific integrated circuit, field programmable gate array, digital circuit, analog circuit, combinations thereof, or other now known or later developed device for reconstructing an image object from detected emissions. The reconstruction processor 26 is a single device, a plurality of devices, or a network. Different devices making up the reconstruction processor 26 may perform different functions, such as one processor (e.g., application specific integrated circuit or field programmable gate array) for reconstructing the object and another (e.g., graphics processing unit) for rendering an image from the reconstructed image object. In one embodiment, the reconstruction processor 26 is the control processor 42 or other processor of the nuclear imaging system 30. In other embodiments, the reconstruction processor 26 is part of a separate workstation or computer. The reconstruction processor 26 is configured by software, firmware, and/or hardware to reconstruct a volume or object from emissions.

The reconstruction processor 26 is configured to reconstruct from the detected emissions. Emission tomography is performed. The anatomy data from the CT/MR system 44 may be used in the reconstruction of the detected emissions. The reconstruction is controlled by one or more settings (e.g., values of variables). The control processor 42, implementing the AAA, outputs the reconstruction, including reconstruction settings. The reconstruction processor 26 performs the reconstruction based on the reconstruction defined by the AAA. One or more settings may be based, at least in part, on information from the MMDQA.

Any reconstruction may be used to estimate the activity concentration or distribution of the tracer in the patient. The reconstruction processor 26 accesses the detected emission events from the memory 36, from the detector 40, or buffers to reconstruct. The anatomy data may likewise be accessed. The detected emissions and anatomy data are used to reconstruct the distribution of the radioisotope in three dimensions. Forward and backward projection are used iteratively until a merit function indicates completion of the reconstruction (i.e., a best or sufficient match of the image object to the detected emissions).

The reconstruction processor 26 generates one or more images based on the reconstruction. Any given image represents the emissions from the patient. The image shows the spatial distribution, such as with a multi-planar reconstruction or a volume rendering. For quantitative imaging, the image represents accurate measures (e.g., in Bq/ml) of the activity concentration. Alternatively or additionally, the image shows a quantity or quantities (e.g., alphanumeric) representing the activity concentration or specific uptake values for one or more locations or regions.

The display 38 is a CRT, LCD, plasma screen, projector, printer, or other output device for showing an image. The display 38 displays an image of the reconstructed functional volume.

The detected anatomy data, emission events, counts, location, scan information (e.g., generic scan settings), inputs, reconstruction settings, system-specific scan settings, patient information, application, or other information are stored in the memory 36. The memory 36 may store data at different stages of processing, such as communications between the control arrangements (e.g., inputs and outputs of AAA, ASA, and/or MMDQA). The data is stored in any format.

The memory 36 is a buffer, cache, RAM, removable media, hard drive, magnetic, optical, database, or other now known or later developed memory. The memory 36 is a single device or group of two or more devices. The memory 36 is part of the nuclear imaging system 30 or a remote workstation or database, such as a PACS memory.

The memory 36 is additionally or alternatively a non-transitory computer readable storage medium with processing instructions. The memory 36 stores data representing instructions executable by the programmed control processor 42 and/or the reconstruction processor 26. The instructions for implementing the processes, methods, and/or techniques discussed herein are provided on non-transitory computer-readable storage media or memories, such as a cache, buffer, RAM, removable media, hard drive, or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for controlling operation of a multi-modal emission tomography system, the method comprising:

receiving an input of a type of emission tomography scan and a goal for the emission tomography scan;

generating, by a first machine-learnt network, first settings for reconstruction parameters and second settings for the emission tomography scan, the generating being based on the type, the goal, and patient information, the second settings being generic to the multi-modal emission tomography system;

determining, by a second machine-learnt network, third settings for the emission tomography scan from the second settings, the third settings being specific to the multi-modal emission tomography system;

detecting, by the multi-modal emission tomography system using the third settings, emissions from a patient; and creating an emission tomography image of the patient from the detected emissions, the generating being a function of the first settings.

2. The method of claim 1 wherein receiving the input comprises receiving the type as an application related to anatomy or disease and receiving the goal as a time, resolution, and/or region of interest.

3. The method of claim 1 wherein receiving the input comprises receiving the input from an ordering physician.

4. The method of claim 1 wherein generating the first and second settings comprises generating based on a weight and a height as the patient information.

5. The method of claim 1 wherein generating the first and second settings comprises generating by the first machine-learnt network comprising a deep-learnt network.

6. The method of claim 1 wherein generating the first settings comprises generating values for a type of reconstruction, a relative contrast-to-resolution, and a stop criterion.

7. The method of claim 1 wherein generating the second settings comprises generating the second settings as generic to different types of emission tomography systems including the emission tomography system.

8. The method of claim 1 wherein generating the second settings comprises generating a scan region, a scan time, a dose, and collimator configuration.

9. The method of claim 1 wherein determining comprises determining the third settings as values for operating the multi-modal emission tomography system, the values including a step size, a spread, and/or a collimator position.

10. The method of claim 1 wherein creating comprises reconstructing from the detected emissions, the reconstructing using the first settings.

11. The method of claim 1 further comprising:

checking, by a third machine-learnt network, a quality of the detected emissions;

re-generating the third settings as a function of the quality and the second settings; and detecting other emissions with the re-generating third settings.

12. The method of claim 11 wherein checking the quality comprises checking a number of counts per view and an orbit of the multi-modal emission tomography system.

13. A nuclear imaging system comprising:

a first processor configured to determine a reconstruction and a scan based on a patient characteristic and an application provided by a physician;

the first processor or a second processor configured to determine settings for scan parameters from the scan;

a detector for detecting signals from a patient using the settings, the settings being specific to the detector;

a reconstruction processor configured to reconstruct an image of the detected signals from the patient with the reconstruction; and a display configured to display the image, wherein the first processor is configured to determine the reconstruction and the scan with a first machine-learnt network, and wherein the first or second processor is configured to determine the settings with a second machine-learnt network.

14. The nuclear imaging system of claim 13 wherein the first processor or the second processor is configured to check the detected signals and re-determine the settings based on the check.

15. A method for controlling operation of a multi-modal emission tomography system, the method comprising:

controlling the multi-modal emission tomography system with: an application analysis module configured to recommend scan information based on a patient state and medical information from a physician, an acquisition set-up module configured to recommend settings for acquisition specific to the multi-modal emission tomography system based on the scan information, and a data quality assessment module configured to feedback to the acquisition set-up module for a change in the settings for the acquisition;

detecting emissions from the patient using the settings; and generating an emission tomography image from the detected emissions.

16. The method of claim 15 wherein controlling comprises controlling with the application analysis module configured to recommend reconstruction settings based on the patient state and the medical information, and wherein generating comprises generating with the reconstruction settings.

17. The method of claim 15 wherein controlling comprises controlling with the data quality assessment module configured to provide the feedback based on the detected emissions.

18. The method of claim 15 wherein controlling comprises controlling with the data quality assessment module configured to output a mitigation.

19. The method of claim 15 wherein controlling comprises controlling with the application analysis module, the acquisition set-up module, and the data quality assessment module each comprising separate machine-learnt networks.

* * * * *